(12) United States Patent
Martin

(10) Patent No.: US 10,694,781 B2
(45) Date of Patent: Jun. 30, 2020

(54) ELECTRONIC PIPE VAPORIZER

(71) Applicant: James Ronald Martin, Hitch Cock, TX (US)

(72) Inventor: James Ronald Martin, Hitch Cock, TX (US)

(*) Notice: Subject to any disclaimer, the term of this patent is extended or adjusted under 35 U.S.C. 154(b) by 0 days.

(21) Appl. No.: 15/289,108

(22) Filed: Oct. 7, 2016

(65) Prior Publication Data
US 2018/0098569 A1  Apr. 12, 2018

(51) Int. Cl.
| | |
|---|---|
| *A24F 47/00* | (2020.01) |
| *A24F 5/06* | (2006.01) |
| *A24F 5/10* | (2006.01) |
| *H01M 10/46* | (2006.01) |
| *H01M 2/10* | (2006.01) |
| *H01M 10/0525* | (2010.01) |
| *A61M 15/06* | (2006.01) |

(52) U.S. Cl.
CPC .............. *A24F 47/002* (2013.01); *A24F 5/06* (2013.01); *A24F 5/10* (2013.01); *A61M 15/06* (2013.01); *H01M 2/1022* (2013.01); *H01M 10/46* (2013.01); *H01M 10/0525* (2013.01); *H01M 2220/30* (2013.01)

(58) Field of Classification Search
CPC ...... A24F 47/002; A24F 47/008; A24F 47/00; A24F 1/00; A24F 5/02; A24F 5/04; A24F 5/06; A24F 5/08; A61M 15/06; A61M 15/00; A61M 11/042; A61M 11/001
See application file for complete search history.

(56) References Cited

U.S. PATENT DOCUMENTS

| | | | |
|---|---|---|---|
| 6,516,796 B1 * | 2/2003 | Cox .................... | A61M 11/042 128/200.23 |
| 7,913,686 B2 * | 3/2011 | Hughes ............... | A61M 15/009 128/200.12 |
| 2010/0200008 A1 * | 8/2010 | Taieb ................... | A24F 47/008 131/360 |
| 2015/0053221 A1 * | 2/2015 | Asghar-Sheikh ..... | A24F 47/008 131/329 |
| 2016/0295919 A1 * | 10/2016 | Thomas, Jr. ......... | A61M 11/042 |

* cited by examiner

*Primary Examiner* — Alex B Efta
(74) *Attorney, Agent, or Firm* — Delphine James

(57) ABSTRACT

The present invention is an electronic pipe vaporizer having the configuration of a conventional pipe with a bowl and a stem. The bowl further comprises an insert configured to receive four color coded atomizers. A control panel in electronic communication with the four color coded atomizers that allow the user to customize the vapor to taste. The upper portion of the insert engages with a tamper ring segment that illuminates when the user takes a puff from the stem.

15 Claims, 4 Drawing Sheets

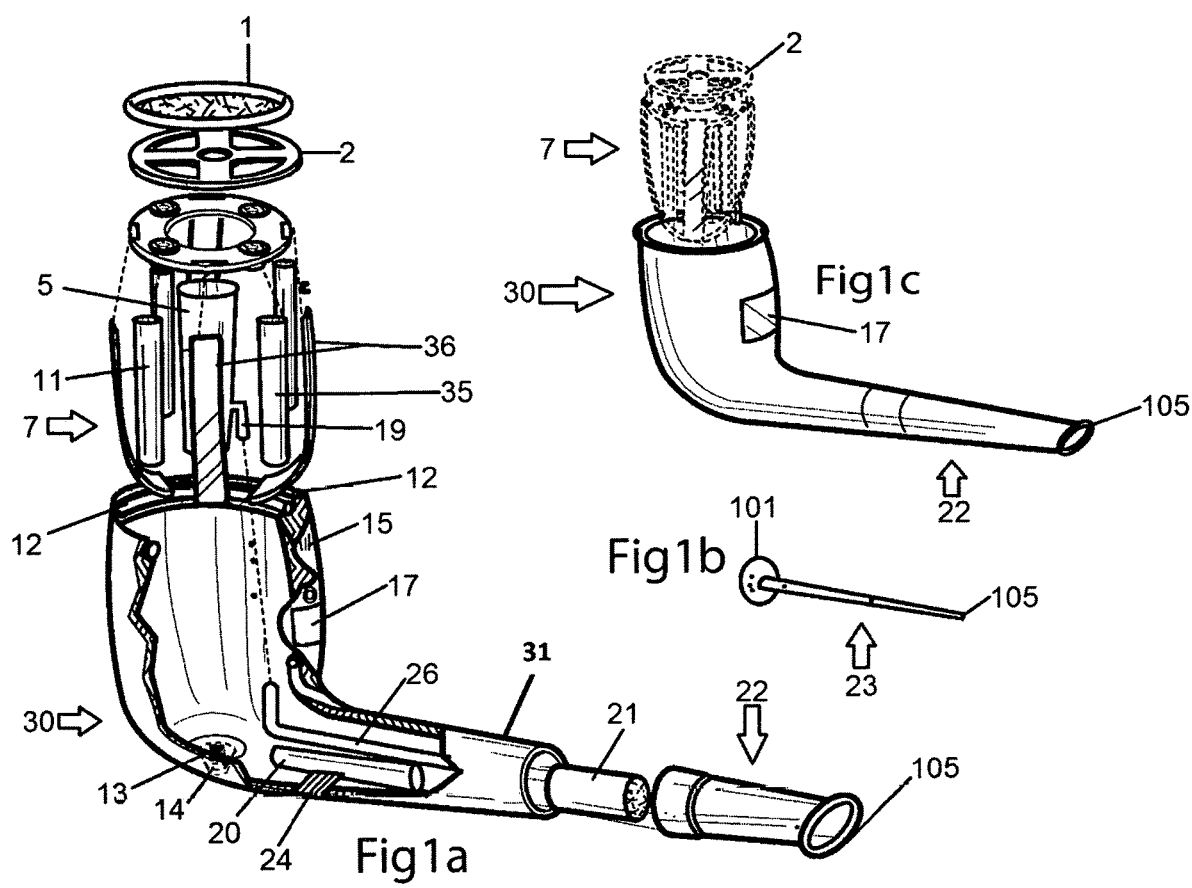

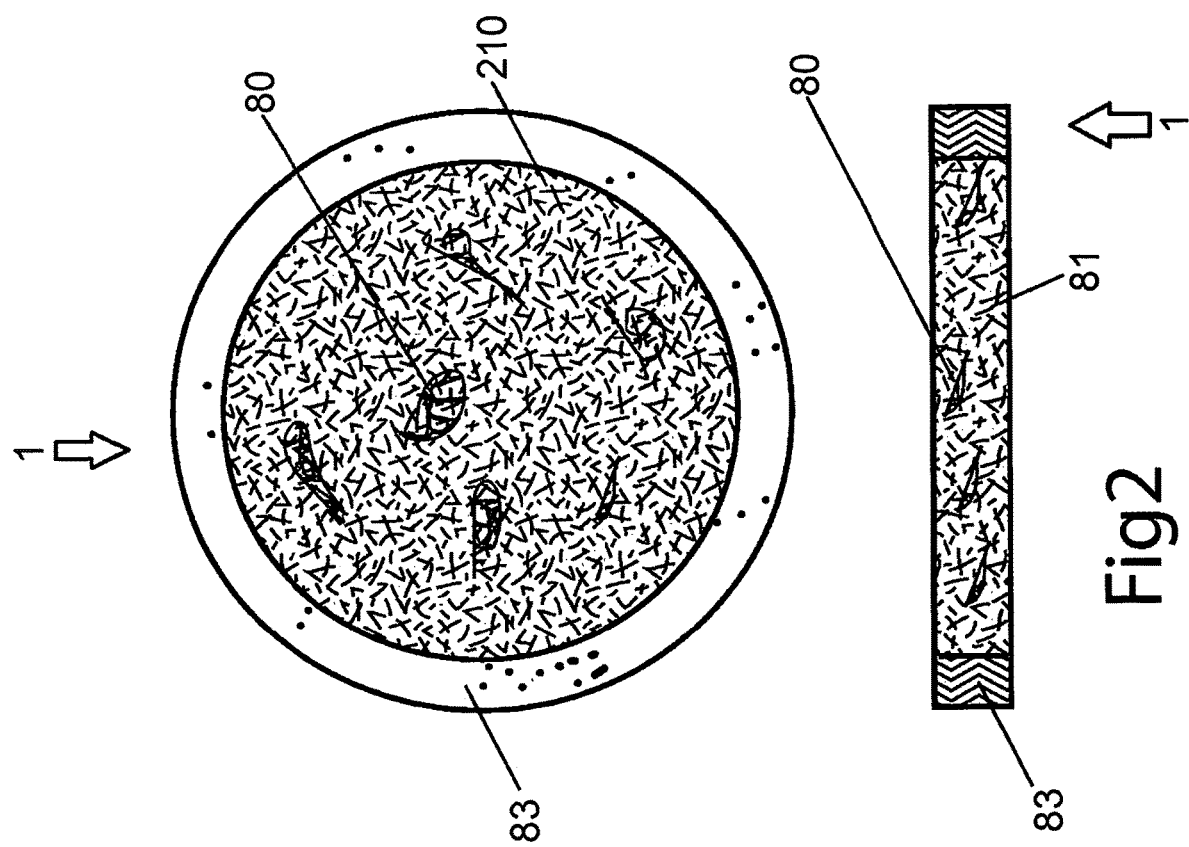

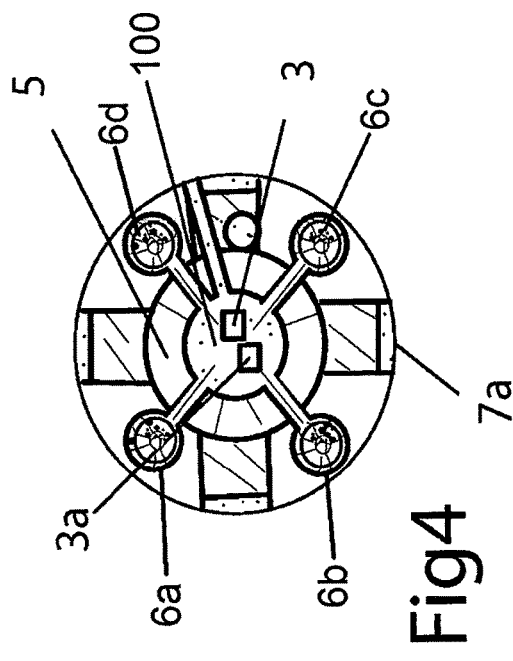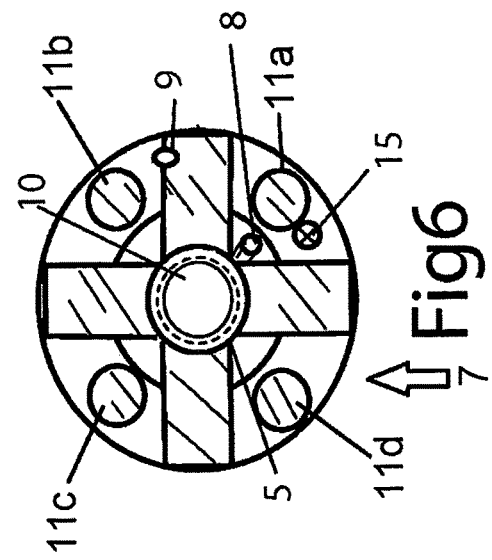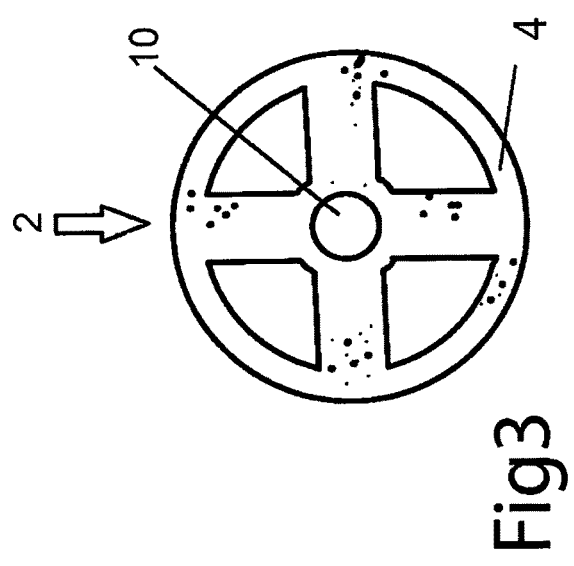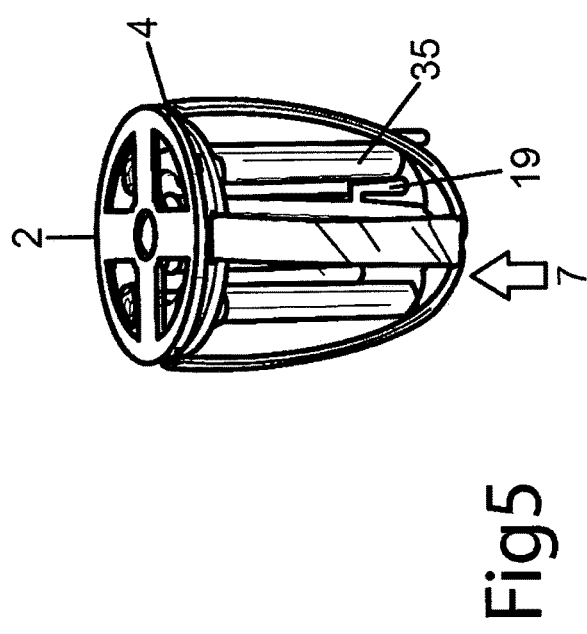

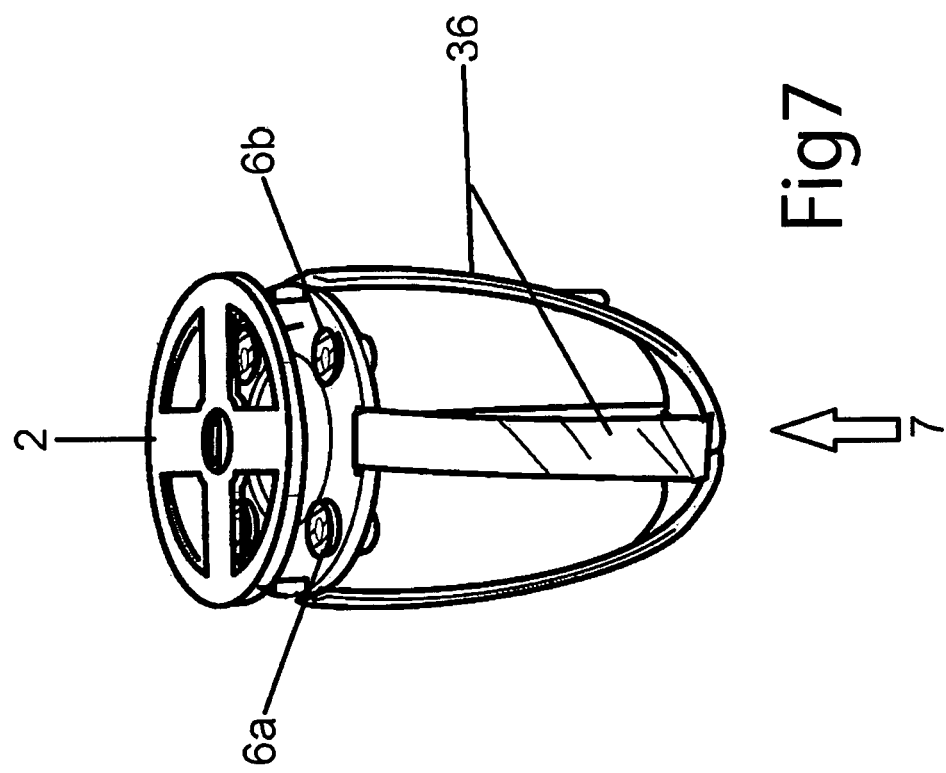

ELECTRONIC PIPE VAPORIZER

This invention claims the benefit of provisional application 62/138,321 and continuation in part of application Ser. No. 15/081,090

BACKGROUND OF THE INVENTION

This invention relates to electronic smoking-substitute devices and in particular to an electronic pipe which allow the user to control the composition of the inhaled vapor.

Conventional smoking devices functions by burning tobacco and releasing smoke containing tar into the air which is inhaled by the user and innocent bystanders. The inhaling of tar tainted vapor released from smoking tobacco is a health and safety hazard linked to lung cancer. As a result public facilities and work places have created smoke free environments. Thus, substitute smoking devices which conceals the vaporizers and allows the user to enjoy an environment free hazard smoking experience is needed.

SUMMARY OF THE INVENTION

One of the main objectives of the present invention is to manufacture an electronic pipe of various designs that can be easily assembled. The electronic pipe has the configuration of a conventional pipe with a bowl, barrel housing and a stem. The bowl comprises a top cap that simulates ash and a red glow burning tobacco utilizing fiber optics. The bowl has four chambers for receiving the following color coded atomizer capsules:
  Flavor capsule
  Aroma capsule
  Caffeine capsule
  Nicotine capsule A control panel in electronic communication with the capsules allows the user to determine the amount of release from each of the 4 capsules into the mixing chamber thereby providing the user with a customized smoking experience through the passageway within the mouthpiece.

The above and other objects, features and advantages of the present invention should become even more readily apparent to those skilled in the art upon a read in of the following detailed description in conjunction with the drawings wherein there is shown and described illustrative embodiments of the invention.

BRIEF DESCRIPTION OF DRAWINGS

These and other details of the present invention will be described in connection with the accompanying drawings, which are not furnished only by way of illustration and not in limitation of the invention.

FIG. 1a is a perspective view of the present invention, the electronic pipe without the electronic insert.

FIG. 1b is a perspective view of the present invention.
FIG. 1c is a cutaway view of the tamping tool.
FIG. 2 illustrates a cross-sectional view of the cap.
FIG. 2A illustrates a top view of the cap.
FIG. 3 illustrates a top view of the tamping ring.
FIG. 4 illustrates a bottom view of the housing insert.
FIG. 5 illustrates a side cutaway view of the housing insert.
FIG. 6 illustrates a bottom view of the housing insert.
FIG. 7 illustrates a side view of the housing insert.

DETAILED DESCRIPTION OF THE INVENTION

Referring to FIG. 1, there is shown a perspective view of the present invention an electronic pipe (35) comprising a conventional stem (22) attached to the lower end of the simulated bowl (30). Stem (22) comprises a passageway (26) extending there through with a saliva filter (21) disposed within the passageway (26) and configured to prevent saliva from entering the simulated bowl (30).

The present invention is manufactured as a kit stored within a specialized container with the kit including a stem (22), simulated bowl (30), tamping ring (2), and removable insert housing (7). The kit can be stored in a decorated box or pouch. The simulated bowl (30) comprises an outer shell casing with a cavity formed therein for receiving the electronic vaporizer (35) simulated components therein. Simulated bowl (30) has the same size and configuration as a conventional pipe bowl. Circumferentially internally disposed within the wall of rim (12) of simulated bowl (30) is a channel (12) for receiving sealing member (4) which can be a conventional O-Ring. Aroma distribution port comprises a plurality of vents (15) are situated within the outer shell casing of bowl (30) allowing vapor to escape there through.

Stem (22) connects at the bottom of barrel housing (31) and extends linearly outward therefrom. Stem (22) is formed from an elongated tubular member with a small bore (26) that extends there through forming the passageway (26) between the mixing chamber (5) and the mouth of a user. The barrel housing (31) is defined by a bottom end with connector member that securely interconnect to base of bowl (30). Barrel housing (31) forms a tubular member that incorporates into the base of the outer shell casing of the simulated bowl (30) wherein the bore passageway (26) extends through the outer shell casing and into the mixing chamber (5) through inhaling port (19). The top end (105) of stem (22) forms the tip of the stem (22) through which the user receives the customized vapor mixture.

Saliva filter (21) can be formed for a mesh, foam or other fibrous material that is disposed within the passageway trapping any saliva from a user mouth within the passageway (26).

FIGS. 3, 4, 5 illustrate an inside view of the removable insert. A removable insert housing (7) is configured to seat within the cavity simulated bowl (30). Insert housing (7) further includes pipe cap (1) disposed atop tamping ring (2). The lower portion of housing insert (7) is configured to seat within the cavity of bowl (30). Housing insert (7) further comprises a centrally located mixing chamber (5) circumferentially surrounded by a plurality of color coded vaporizer chambers (11). Annular outer ring (4) circumferentially surrounds the upper end of housing insert (7) and has a diameter substantially equivalent to rim (12) of the cavity of simulated bowl (30). The mixing chamber (5) and each of the plurality of vaporizer chambers (11) forms a compartment for receiving a color coded capsule. Each chamber (11) extends linearly downwardly towards the base of cavity of the simulated bowl (30). Chambers (11) has a stem retainer (25) for securing color coded capsules therein along with regulator (6). When the mixing chamber (5) is puffed, regulator (6) delivers the user's blend in an amount equal to a single draw of a cigarette. The mix selection is then drawn through the mixing chamber (5).

The oring seat (4) is a channel surrounding the upper end of the insert housing (7) and receives the tamping ring (2) which illuminates as a customer takes a puff through the stem (22). There is a reddish orange light element (3) that gives the illusion of burning tobacco for the user. Oring (12) engages with Oring seat (4) at the upper end of simulated bowl (30). A plurality of disjoined slits (15) emanates from outer surface of bowl (30) near channel (12). The outer peripheral edge of pipe cap (1) is disposed above oring seat (4). The tamping ring (2) has a centrally located opening above the mixing chamber (5) through which the light emanates.

Each color coded chamber (11) is configured to receive and operationally engage a specific color coded capsule. Control panel (17) is electronically connected to each color coded atomizer allowing the user to customize the amount of vapor release through each color coded atomizer (11). The capsule connects with the aroma distribution port (15) to release the aroma. Control panel switch (16) is the switch that powers the control panel (17) on/off.

The ejection element comprises an ejection port (14) and spring (13). The ejection spring (13) seats within base of the cavity below the insert housing (7). Ejection port (14) is disposed at the base of the cavity of the simulated bowl (30) below ejection spring (13) and provides an internal compartment for the push pin notch (10) to securely engage therein. The lower portion of the push pin notch (10) extends outward from the ejection port (14) and through the outer casing of the simulated bowl (30) and is operationally engaged with the ejection spring (13) securing the insert housing (7) therein. When push pin notch (10) is depressed within the ejection port (14) the ejection spring (13) expands upward causing insert housing (7) to clear the O-Ring and eject from the cavity of simulated bowl (30).

As depicted, system plug (9) internally disposed near base of housing insert (7) (30) adjacent push pin notch (10) and includes a memory chip, a battery recharge connection along with an electronic connection to the mixing chamber (5), color coded chambers (11a, b, c, and d), and control panel (17). The memory chip supports the electronic capability of the control panel (17) by controlling and storing the user customized programming information. The memory chip is in electronic communication with the mixing chamber (5) and regulator (6) thereby allowing the user to customize the selection within mixing chamber (5). The USB recharge connection (20) allows the user to recharge the power source (i.e. battery (24).

As illustrated pipe cap (1) is disposed atop tamping ring (2). Pipe cap (1) comprises a circular plate with fiber optics (210) incorporated therein configured to illuminate and simulate burning ashes (80). Pipe cap (1) is circular and has a diameter substantially equivalent to the diameter of the cavity of the simulated bowl (30).

As shown tamping ring (2) seats within a channel disposed within the upper end of housing insert (7). FIGS. 2 and 2A illustrate ring (83) that encircles the pipe cap (1) with simulated ash (80) disposed therein. Fiber optics (210) is operationally engaged within simulated ash (80) and in electronic communication with power supply. The peripheral ring (83) can be further comprise fiber optics (210) incorporated therein.

The electronic vaporizer (35) can be manufactured in the Sherlock pipe configuration, Bavarian configuration, Macarthur pipe configuration and Westerner pipe configuration respectively. All of the foregoing pipes configurations can be manufactured with the simulated bowl (30), saliva filter (21), and stem (22) illustrated in FIG. 1.

An inhaler port (19) extends from the mixing chamber (5) into the passageway of the stem (22). As shown inhaler port (19) is a small tubular member which interconnects with inhaler tube connector (8) disposed at the lower end of the mixing chamber (5). Bore (26) provides a passageway from the mixing chamber (5) into stem (22) of the customized vapor of the user.

Insert housing (7) comprises a central mixing chamber (5) surrounded by a plurality of chambers (11) for receiving vapor capsule atomizers therein. The plurality of vaporizer chambers further comprises a plurality of color coded chambers (11a, 11b, 11c, and 11d) configured to operationally engage with a plurality of corresponding color coded capsules. Each capsule contains pressurized gas therein which delivery is controlled by the user selection process (11).

The insert housing (7) has four color coded chambers encircling mixing chamber (5) for receiving the following atomizer capsules:

Flavor capsule
Aroma capsule
Caffeine capsule
Nicotine capsule

The user simulates a puff by programming the control panel (17) as follows:

Flavor capsule and Aroma Capsule is turned on/off
Caffeine capsule is 0 to 100%
Nicotine Capsule is 0 to 100%
The mixture of the caffeine and nicotine is interdependent with one another and must be equal to 100%

To install capsules (11a, b, c and d) the housing insert (7) is turned over and each capsule is inserted into the corresponding regulator (6a, b, c and d). The control panel (17) is in electronic communication with each regulator (6a, b, c and d) to disperse the correct amount of mixture as programmed by the user.

FIG. 3 is a top view of the tamping ring (2) that seats atop the housing insert (7) above the O-Ring (4). The top of the housing insert (7) has a T shape with a central opening for the lighting element (3 and 3a) to illuminate there through. FIG. 4 is a bottom view of the housing insert (7) below the O-Ring (4). FIG. 6 is a top view of the housing insert (7) and FIG. 5 is a cutaway view of the housing insert (7). As depicted 11A, 11B, 11C, and 11D are color coded chambers surrounding the mixing chamber (5) containing pressurized gas. As illustrated, spaced apart arms (36) is a bar that extends curvi-linearly downward the length of the housing insert (7).

When the diaphragm exerts pressure on the capsules the gas is released into the mixing chamber (5). The regulator in combination with the diaphragm controls the delivery of the user selected amount of mixture into the mixing chamber (5). Regulator (a, b, c, and d) dispenses the pressurized vapor according to the blend instructions electronically sent by the control panel (17). The regulator (6) delivers the user's electronically controlled blend in an amount equal to a single draw of a cigarette, into the mixing chamber (5) as a user puffs on stem (22).

A control panel (17) is operationally incorporated within the outer casing of simulated bowl (30) and is in electronic communication with the plurality of regulators (6) within capsules (11) allowing a user to customize the vapor composition released into the mixing chamber (5). Through the control panel (17) a user determines the amount released into the mixing chamber (5). A power supply is in electronic communication with the control panel (17), the tamping ring (2) and pipe cap (1). The electronic vaporizer (35) can be powered by a rechargeable lithium-ion battery located below the simulated bowl (30) just before the saliva filter (21).

Alternatively a mini-USB port (20) can be incorporated within the base of bowl (30) for conventional charging of battery (24).

When the housing insert (7) slides into the simulated bowl (30) it makes simultaneous connections. The inside cavity of the simulated bowl (30) must be sealed so that no diluting air enters the system. The tamper tool (23) comprises a shaft with a pointed end (107) on one side and a small flat plate on the opposite side. The flat plate (101) of tamper/pushpin tool (23) can be used upon tamper ring (2) to ease the O-ring (4) to seat and interlock within channel (12). As the insert (7) moves into position within the bowl (30) the aroma capsule connects with the aroma distribution port (15), the system plug insert (9) interconnects with its mating portion pipe system plug (18) within the simulated bowl (30), the upper end of the inhaler tube (19) interconnects with the mixing chamber (5) which then extends laterally through passageway (26) to the saliva filter (21). As these connections occurs the ejection spring (13) is simultaneously depressed by the pushpin notch (10) above the ejection port (14).

To remove the insert housing (7), the end of the tamper/pushpin tool (23) engages with the pushpin (10) through the ejection port (14) to disengage the ejection spring (13). The disengagement of the ejection spring (13) causes all of the connections to disengage thereby moving the insert housing (7) upward and releasing the pipe cap (1).

Each of the pressurized chamber contains a pre-determined amount of "flavored gas". The housing further comprises a compartment incorporated within a section inner wall of the housing for holding a power source that is electrically connected to the user control mechanism. The bowl has a surrounding wall that extends upward to the opening.

The insert assembly further comprises a cap having an outer perimeter configured to operationally couple within an upper inner annular wall of the bowl as the insert assembly operationally engages within the bowl.

The insert assembly further comprises a light source operationally coupled to a light controller with both disposed beneath the cap above the mixing chamber such that when the a draw is taken from the draw end the light controller activates the light source to illuminate.

The cap further comprises an inner wall that illuminates and simulates ashes burning when the draw is taken from the draw end.

A sealing member is configured to seat within an annular channel that circumferentially internally surround the upper end of the bowl between the annular wall and the outer perimeter of the cap thereby sealing the cap within the bowl. Each of the plurality of pressurized chambers are designated a unique pre-determined color code.

What is claimed is:

1. An electronic smoking device comprising:
an insert assembly and a housing that simulates a conventional smoking pipe having a bowl attached to a smoking tube and adapted to receive the insert assembly therein; the bowl having a cavity defining a surrounding wall and a top opening opposite a bottom wall; a lower end of the surrounding wall forming a bore directly linked to a passageway disposed through the smoking tube that laterally extends to a draw end; allowing gaseous vapor flow from the bowl through draw end, the insert assembly comprising a collar with an equivalent diameter to the top opening of the bowl and is surrounded by a plurality of spaced apart bars that extending linearly downward to a bottom section wherein a cage is formed; the cage of the insert assembly encircling an opened mixing chamber surrounded by a plurality of pressurized chambers with each pressurized chamber containing. a pre-determined amount of flavored gas therein; a connection member internally mounted within the bottom wall of the bowl, the bottom section of the insert assembly configured to operationally couple with the connection member when internally inserted into the pipe bowl, each pressurized chamber operationally coupled to a regulator that controls a synchronized release of a customized amount of the flavored gas from each pressurized chamber therefrom into the mixing chamber; the gaseous vapor formed within the mixing chamber from the predetermined amount of each of the flavored gas released from each pressurized chamber upon a draw from the draw end; each regulator mounted to the collar of the cage; and a user control mechanism electronically connected to the regulator allowing a user to selectively control the pre-determined amount of the flavored gas released into the mixing chamber upon the draw from the draw end.

2. The electronic smoking device of claim 1 wherein the housing further comprises a compartment incorporated within a section of a surrounding wall of the housing for holding a power source that is electrically connected to the user control mechanism.

3. The electronic smoking device of claim 2 further comprising a charge port disposed within the compartment electrically interconnecting the power source to an electrical recharging unit thereby allowing the power source to be recharged.

4. The electronic smoking device of claim 1 wherein the insert assembly further comprises a cap having an outer perimeter configured to operationally couple within an upper inner annular wall of the bowl as the insert assembly operationally engages within the bowl.

5. The electronic smoking device of claim 4 wherein the insert assembly further comprises a light source operationally coupled to a light controller with both disposed beneath the cap above the mixing chamber such that when the a draw is taken from the draw end the light controller activates the light source to illuminate.

6. The electronic smoking device of claim 4 wherein the cap further comprises an inner wall that illuminates and simulates ashes burning when the draw is taken from the draw end.

7. The electronic smoking device of claim 4 further comprising a sealing member configured to seat within an annular channel that circumferentially internally surround the upper end of the bowl between the annular wall and the outer perimeter of the cap thereby sealing the cap within the bowl.

8. The electronic smoking device of claim 6 wherein a plurality of fiber optics are electrically connected within the inner wall of the cap.

9. The electronic smoking device of claim 8 wherein the light source is situated below the cap and is electrically connected to the fiber optics wherein upon a draw from the draw end simulated ash is displayed within the cap.

10. The electronic smoking device of claim 1 wherein the housing further comprises an aroma port disposed within an internal section of the surrounding wall and is operationally coupled to a pressurized gas chamber containing an aroma gas and is in fluid communications therewith allowing the flavored gas to escape therefrom.

11. The electronic smoking device of claim 1 wherein the flavored gas is from the group consisting of nicotine, caffeine, inert gas, or an aroma gas.

12. The electronic smoking device of claim 1 wherein each of the plurality of pressurized chambers are designated a unique pre-determined color code.

13. The electronic smoking device of claim 11 wherein the customized amount of flavored gas has a combination of nicotine and caffeine that equals 100%.

14. The electronic smoking device of claim 4 further comprising a hole through the bottom wall of the bowl leading directly to the connector member.

15. The electronic smoking device of claim 14 further comprising a tamping tool for inserting/releasing the insert from the bowl, the tool comprising:

a shaft having a pointed end directly opposite a flat plate end; the pointed end configured to be inserted through the hole through the bottom wall of the bowl located proximately near the connection member allowing the insert assembly to be releasable disconnected therefrom, a flat plate configured to tap upon the wall of the cap allowing the connector member to securely interconnect as the insert assembly is inserted therein.

\* \* \* \* \*